United States Patent [19]

Matthews et al.

[11] 3,939,123
[45] Feb. 17, 1976

[54] LIGHTLY CROSS-LINKED POLYURETHANE HYDROGELS BASED ON POLY(ALKYLENE ETHER) POLYOLS

[75] Inventors: Virgil Edison Matthews, Charleston; Robert John Knopf, Saint Albans, both of W. Va.

[73] Assignee: Union Carbide Corporation, New York, N.Y.

[22] Filed: June 18, 1974

[21] Appl. No.: 480,568

[52] U.S. Cl. ............... 260/77.5 AM; 260/2.5 AD; 260/2.5 AY; 260/77.5 AP
[51] Int. Cl.² ................. C08G 18/66; C08G 18/14
[58] Field of Search 260/77.5 AN, 77.5 AP, 2.5 AD, 260/2.5 AY, 77.5 AM; 11/33.8 JB; 161/159

[56] References Cited
UNITED STATES PATENTS

| | | | |
|---|---|---|---|
| 3,164,565 | 1/1965 | Calamari | 260/33.8 JB |
| 3,627,714 | 12/1971 | Merkl | 260/77.5 AM |
| 3,694,301 | 9/1972 | Gruenewald | 161/159 |
| 3,778,390 | 12/1973 | Ulrich | 260/2.5 AN |
| 3,821,136 | 6/1974 | Hudgin | 260/77.5 AP |
| 3,822,238 | 7/1974 | Blair | 260/2.5 AD |

*Primary Examiner*—H. S. Cockeram
*Attorney, Agent, or Firm*—Francis M. Fazio

[57] ABSTRACT

Polyurethane hydrogels of high water swellability comprising lightly crosslinked polymers of isocyanate terminated prepolymers which are the reaction production of (i) poly(alkyleneoxy) polyols with (ii) organic diisocyanates that has been lightly crosslinked with (iii) water or an organic polyamine.

45 Claims, No Drawings

LIGHTLY CROSS-LINKED POLYURETHANE HYDROGELS BASED ON POLY(ALKYLENE ETHER) POLYOLS

BACKGROUND OF THE INVENTION

The use of fibrous materials as absorbents for moisture is a well known, widespread practice. In this application many of the natural and synthetic fibers have been used and extensive efforts have been made to improve the absorption properties of the materials. One of the major deficiencies of the natural and synthetic materials heretofore used has been the tendency for them to release the absorbed moisture when pressure has been applied to the moisture containing material. The fact that pressure causes the absorbed fluid to be expelled from the fibers is known as reversible absorption. For many applications, however, irreversible absorption is desired, for example, in surgical dressings, diapers, bed pads, catamenials, and the like, whereby the absorbed moisture is retained in the absorbent material under an applied pressure.

Within the past few years recent innovations have resulted in the production of materials having such irreversible absorption properties; these materials are now known as hydrogels. In most instances they have been produced in powder or particulate form and even, in some instances, in film form. An especially interesting characteristic of the hydrogel polymers is that when in contact with water they absorb it and swell to a certain point and stop and the final swollen polymer is still similar in shape to its initial unswollen shape. Many of the hydrogels have the ability to absorb many times their original weight in water without becoming soggy or deformed. In general, the hydrogels are used in conjunction with other materials as supports. Among the U.S. patents that have issued in this field are U.S. Pat. Nos. 3,669,103; 3,589,364; 3,694,301; 3,670,731; and 3,164,565. This is but an exemplary listing and should not be considered complete.

SUMMARY OF THE INVENTION

Water swellable, lightly crosslinked, hydrogel polymers of an isocyanato terminated prepolymer comprising the reaction product of (i) poly(alkyleneoxy) polyol having an average molecular weight up to about 25,000 with (ii) organic diisocyanate wherein said prepolymer is lightly crosslinked with (iii) a crosslinking agent that is water or an organic polyamine, the amount of crosslinking agent used being an equivalent amount based on the number of equivalents of isocyanato groups present in the prepolymer.

DESCRIPTION OF THE INVENTION

The poly(alkyleneoxy) polyols that are used in producing the hydrogel polymers of the present invention are those having a molecular weight up to about 25,000. These polyols can be diols, triols or tetrols, with the molecular weight of the polyol varying depending upon which is used.

The suitable diols are the poly(ethyleneoxy) glycols which have a molecular weight of from about 4,000 to 25,000, preferably from about 6,000 to 20,000. These diols are well known and many are commercially available. Minor amounts, preferably up to about 35 weight percent of a poly(propyleneoxy) glycol or a poly(butyleneoxy) glycol can also be present. The polyols can be block or random copolymers containing mixtures of ethyleneoxy, propyleneoxy, or butyleneoxy units.

The triols and tetrols that can be used are those having a molecular weight of from about 92 to 5,000, preferably from about 500 to 1,500. These can be the poly(alkyleneoxy) polyols wherein the alkyleneoxy group contains 2 to 4 carbon atoms and they can be homopolymers or block or random copolymers having three or four reactive hydroxyl groups. One can also use the aliphatic polyhydroxyl compounds of the formula $C_nH_{2n+2-m}(OH)_m$ wherein $n$ is an integer having a value of from 3 to 6 and $m$ has a value of 3 or 4.

Illustrative of the suitable polyols are poly(ethyleneoxy) diol, poly(propyleneoxy) diol, poly(butyleneoxy) diol, copoly(ethyleneoxy-propyleneoxy) diol, poly(ethyleneoxy) triol, poly(ethyleneoxy) tetrol, poly(propyleneoxy) triol, copoly(ethyleneoxy-propyleneoxy) triol, copoly(ethyleneoxy-butyleneoxy) triol, glycerine, sorbitol, 1,2,6-hexanetriol, trimethylolpropane, pentaerythritol, dipentaerythritol, and the like. The alkylene adducts of the mono or polyamines such as ethylamine, ethanolamine, diethanolamine, ethylene-diamine, propylenediamine, isopropanolamine, hexamethylenediamine, and the like. Mixtures thereof can be used if desired. In addition, one can include some polycaprolactonepolyol, or conventional polyester polyol.

The hydrogels can be produced by reacting the poly(alkyleneoxy) diol with an organic diisocyanate to form an isocyanato terminated prepolymer which is then lightly crosslinked with a crosslinking agent that is a mixture of an organic diamine and an organic triamine. In another embodiment, the hydrogels can be produced by reacting a mixture of poly(alkyleneoxy) diols and poly(alkyleneoxy) triols and/or tetrols with an organic diisocyanate to form the prepolymer which is then lightly crosslinked with a crosslinking agent that is water, an organic diamine, or a mixture thereof. When a mixture of polyols is used in producing the hydrogels the mole ratio of the diol to the higher polyols is at least about 6:1 and can be as high as about 40:1. Preferably this mole ratio is from about 15:1 to about 30:1, and more preferably from about 20:1 to about 25:1. It has been observed that the mole ratio of diol to higher polyol has an effect on water uptake; the higher the mole ratio, the higher the water uptake.

Any of the known organic diisocyanates can be used in the reaction with the polyol to produce the isocyanato terminated prepolymer. These isocyanates are well known to those skilled in the polyurethane art and illustrative thereof one can mention, tolylene diisocyanate, phenylene diisocyanate, hexamethylene diisocyanate, isophorone diisocyanate, methylenebis(4-phenylisocyanate), 4,4'-methylene bis(cyclohexylisocyanate), 4,4'-methylene bis(o-tolylene isocyanate), dimer acid diisocyanate, 4,4'-methylene bis(phenyleneisocyanate), 2,2,4-trimethylpentane diisocyanate, aniline-formaldehyde polyisocyanates having an average of from about two to about three isocyanato groups per molecule.

In producing the isocyanato terminated prepolymer one reacts an excess of the isocyanate with the polyol. The ratio of isocyanato groups to hydroxyl is from about 1.2 to 1.6 equivalents of isocyanato per equivalent of hydroxyl. An equivalent amount of isocyanato sufficient to react with any water present in the reactants can also be added. It has been observed that at lower ratios the hydrogel polymer becomes too soluble, while at ratios above 1.6:1 the water uptake of the hydrogel decreases. In this reaction any of the known catalysts can be used such as dibutyltin dilaurate, stannous octoate, triethylenediamine, lead octoate, bis(-dimethylamino) ethyl ether, and the like. The catalyst is present at a concentration of from about 0.001 to about 1 percent by weight. The conventional catalytic amounts are employed.

Production of the isocyanato terminated prepolymer is carried out in the presence of an inert organic solvent such as benzene, toluene, trichloroethane, trichloroethylene, bis(2-chloroethyl) ether, methyl ethyl ketone, ethylene dichloride, ethyl acetate, xylene, and the like.

The temperature at which the prepolymer is produced can vary from about 50°C. to about 170°C. and is not critical to the reaction. The time required to carry the reaction the completion will vary depending upon the particular reactants and catalyst used, the size of the batch and other factors known to those skilled in the art. The reaction for the preparation of the prepolymer is preferably carried out under anhydrous conditions and under an inert gas atmosphere.

The product obtained in this first step is an isocyanato terminated prepolymer that is soluble in the organic solvent used in carrying out the reaction. This solution has a solids content dependent upon the amount of materials initially charged. For ease in further handling it is preferred that the solids content be not greater than about 40 weight percent, preferably from 25 to 35 weight percent. The solution viscosity should range from about 15,000 to about 200,000 centipoises.

To produce the hydrogel polymer from the above isocyanato terminated prepolymer, one reacts this prepolymer with a crosslinking agent to effect a light degree of crosslinking. The term lightly crosslinked hydrogel polymer signifies a hydrogel that contains not more than an average of about one crosslink unit per 50,000 average molecular weight of the hydrogel. Preferably there is an average of about one crosslink unit for each 100,000 to 300,000 hydrogel molecular weight and more preferably about one crosslink unit for each 150,000 to 250,000 hydrogel molecular weight. As previously indicated, the suitable crosslinkers are water or the organic polyamines, such as the primary or secondary diamines or triamines. The polyamines can be any of the known aliphatic or aromatic polyamines such as ethylene diamine, diethylene triamine, propylene diamine, hexamethylene diamine, methylene bis(aniline), tolylene diamine, isophorone diamine, trimethylpentane diamine, aniline-formaldehyde adduct polyamines, and the like. The amount of crosslinking agent used is an amount sufficient to react with all of the terminal isocyanato groups and to effect a light crosslinking. The desired concentration of crosslinker is that wherein the equivalents of reactive crosslinking groups in the crosslinking agent used is equivalent to the number of equivalents of isocyanato groups present in the prepolymer. This amount should be sufficient to react with all of the isocyanato groups and crosslink the polymer but it should not be an amount which would result in end-capping of the isocyanato groups rather than crosslinking.

The following examples further serve to illustrate this invention.

EXAMPLE 1

A mixture was prepared containing 400 grams of poly(ethyleneoxy) diol having an average molecular weight of about 8,565 and 1,650 grams of benzene. Analysis indicated that this solution contained 2.14 grams of water. Then 32.93 grams of a 80:20 mixture of 2,4- and 2,6- tolylene diisocyanate were added. This amount is sufficient to provide an isocyanato/hydroxyl equivalent ratio of 1.5:1 and an isocyanato/water equivalent ratio of 1:1. Six drops of dibutyltin dilaurate catalyst were added and the mixture was heated at 70°C. to 78°C. for 3.5 hours under a nitrogen atmosphere. At the end of the reaction the isocyanato terminated prepolymer was analyzed for free isocyanato groups.

A 907.5 gram portion of the solution, containing 0.0559 equivalent of isocyanato group, was reacted at ambient temperature, under nitrogen, with a mixture of 0.6549 gram of diethylene triamine and 1.1420 grams of a 90/10 weight percent blend of ethylene diamine and 1,3-diaminopropane dissolved in 50 grams of benzene. This amines solution contained 0.056 equivalent of amino group. The entire mixture gelled within one minute after mixing.

The gel was covered with n-hexane and triturated to yield a white granular solid and a colorless gel, both of which were recovered as separate portions and dried in a vacuum oven. The dried white granular hydrogel polymer absorbed 20.6 times its weight of water upon immersion in water for 42 hours. Analysis also indicated that it was water soluble to the extent of 18.5 weight percent.

A sample of the dried white gel portion absorbed 10.6 times its weight of water and dissolved to the extent of 13 percent by weight when immersed in water for 24 hours at room temperature.

EXAMPLE 2

A mixture containing 200 grams of the same poly-(ethyleneoxy) diol used in Example 1, 3.08 grams of a poly(oxyethylene) triol having an average molecular weight of about 1,190 and 611 grams of benzene was azeotropically distilled to remove 50 ml. of distillate. Analysis of the residual solution showed it to contain only 0.002 weight percent water. The dry mixture remaining in the reactor contained 180 grams of the diol, 2.77 grams of the triol and 550 grams of benzene. In this solution, the diol:triol molar ratio was 9:1. A solution of 7.21 grams of methylene bis(4-phenylisocyanate) in 50 grams of benzene (isocyanato/hydroxyl equivalent ratio of 1.33:1) was added to the polyol solution after the addition of 2 drops of dibutyltin dilaurate. The reaction began, as evidenced by a thickening of the solution. The reaction was continued at reflux after adding an additional 200 grams of benzene. The solution was diluted with another 100 grams of benzene and it was used to cast 9 films, 50 mils thick, on glass plates. These films were divided into three groups of three plates each to study the methods by which the isocyanato terminated prepolymer could be crosslinked to the hydrogel polymer.

Group A — The three coated plates in this group were placed in a forced air oven which also contained a beaker filled with 300 ml. of water. The films were heated at 75°C. for 45.25 hours, the plates removed and the films peeled off. Two of the films were only partially cured; the third was tough and hard. When immersed in water the third film showed a water uptake equal to 30 times its weight and was soluble to the extent of 57 percent by weight. The water solubility indicates that partial crosslinking had occurred, however; the lightly crosslinked polymer was a hydrogel having a high water absorbency.

Group B — This group of coated plates was placed in a vacuum oven which also contained a beaker containing one gram of ethylene diamine. The oven was evacuated, sealed and maintained at a temperature of 42°C. for 46 hours. The films were then recovered from the plates. While these films were tough they were completely soluble in water, an indication that crosslinking had not occurred and that the high amine concentration present had resulted in end-capping rather than crosslinking.

Group C — This group of plates was left standing at ambient room conditions for 46 hours, permitting crosslinking to occur by means of atmospheric moisture. The hard, tough hydrogel polymers produced absorbed 12.5 times their weight of water and were water soluble to the extent of 0.5 weight percent. These results indicate extensive crosslinking as evidenced by the low water solubility and the lower water absorbency as compared to the films obtained in Group A.

The results show the need for careful control of crosslinking agent in order to obtain a good hydrogel of high water absorbency and low water solubility.

EXAMPLE 3

A solution containing 100 grams of the same diol and 0.5876 gram of the same triol of Example 2 and 518 grams of benzene was distilled until the distillate was no longer cloudy, 160 ml. of distillate were removed. Analysis of a 131.9 gram sample showed a residual water content in the solution in the reactor of 0.008 weight percent.

At this point the reactor contained 74.27 grams of the diol, 0.4186 gram of the triol and 305.8 grams of benzene; this is a diol to triol mole ratio of 24.6:1. The solution was heated to reflux and while stirring a solution of 3.31 grams of 98 percent methylenebis(4-phenylisocyanate) in 20 grams of benzene was added; isocyanato to hydroxyl ratio of 1.3:1. Three drops of dibutyltin dilaurate were added and the solution stirred at reflux for 45 minutes. At the end of this time, analysis showed an isocyanato equivalent weight of 77,970 for the isocyanato terminated prepolymer solution. The solids content of the solution was about 19.3 weight percent. Four films were cast on glass plates, each 50 mil thick, divided into two equal groups and treated as follows:

Group A — Two of the plates were placed in a forced air oven, which also contained a beaker of water, and left there for 19.75 hours at 52°C. At the end of this period, the films of the lightly crosslinked hydrogel were removed from the plates; they were fully cured and were hard, tough and opaque in appearance. Samples immersed in water for 8 hours showed a water absorption capacity of 35.9 times the weight of the original film. The film was also soluble to the extent of 49.5 weight percent.

Group B — The 2 coated plates in this group were left at ambient room conditions for 50.25 hours, then the films were removed and evaluated. They were hard and tough hydrogel polymer films which showed water absorption capacity of 40.2 times their original weight and a water solubility of 13 weight percent. Portions of these films immersed in 0.3 N sodium chloride solution showed absorption capacities of 41.2 times their weight. This is an indication that the hydrogel polymers of this invention can be used for salt containing solutions as well as water alone.

Portions of the original fluid prepolymer solution aged at room temperature under a nitrogen atmosphere for three days became very thick and viscous. Analysis of this material indicated an isocyanato equivalent weight of 793,000. Films produced from this material by the two procedures disclosed above were completely soluble in water indicating that unknown reactions occur on standing that destroy the terminal isocyanato groups and render the prepolymer unsuitable for the production of the lightly crosslinked hydrogel polymers of this invention.

EXAMPLE 4

Following the procedure described in Example 3, an isocyanato terminated prepolymer solution was produced by reacting a mixture of 180.65 grams of the same diol and 1.07 grams of the same triol with 7.37 grams of methylene bis(4-phenylisocyanate) in 755 grams of benzene. In this reaction the diol to triol molar ratio was 23.4:1 and isocyanato to hydroxyl equivalent ratio was 1.2:1. The catalyst used was 2 drops of dibutyltin dilaurate. This prepolymer solution was a fluid liquid having a 20% by weight solids content. Films of about 50 mils thickness were cast on glass plates. One group of these films was cured for 20 hours at 75°C. in a forced air oven that also contained a beaker of water. The films completely dissolved in water upon immersion over night indicating that end-capping had resulted and that the prepolymer had not been converted to a lightly crosslinked hydrogel polymer, because of the large excess of water crosslinking agent present. The second group was cured for 93 hours at ambient room conditions; however, it was noted that the films were hard and free of benzene odor after only 24 hours of exposure. The cured films were lightly crosslinked hydrogels having a water uptake of 33.4 times their weight and they were soluble in water to the extent of 33%. These results indicated that a lightly crosslinked hydrogel polymer had been produced in this second group.

EXAMPLE 5

Following the procedure described in Example 3, an isocyanato terminated prepolymer was produced by dissolving 200 grams of the same diol and 1.19 grams of the same triol of Example 2 in 905 grams of benzene. This was azeotropically distilled to remove 130.7 grams of distillate. A 109.6 grams sample of the dry solution was removed for water analysis, which was found to be 0.0061%. The remaining solution, which now contained 174.87 grams of the diol, 1.04 grams of the triol and 587.1 grams of benzene was heated to 44°C. and a solution of 9.01 grams of methylene bis(4-phenylisocyanate) in 153 grams of anhydrous benzene and 2 drops of dibutyltin dilaurate were added. This mixture had a diol to triol molar ratio of 23.4:1 and an isocyanate to hydroxyl equivalent ratio of 1.6:1. After stirring at reflux for 2 hours the isocyanato terminated prepolymer solution was left standing over night at room temperature under a nitrogen atmosphere. This prepolymer solution was used to prepare casts films on glass plates. A film that was 10 mils thick when cast and was permitted to stand at room temperature for 48 hours using atmospheric moisture as the crosslinking agent produced a lightly crosslinked hydrogel that had a water absorbency of 21 times its weight and a solubility in water of 6.5 weight percent upon immersion in distilled water at room temperature for 24 hours. These results indicated the production of a satisfactory lightly crosslinked hydrogel. A second film that was 50 mils thick when cast was crosslinked at 60°C. in an oven containing a beaker of water over a 5 hour period. The hydrogel polymer film produced in this instance had a water absorbency of 20.7 times its weight and a water solubility of 0.5 weight percent by the same procedure described previously. A third film which was 50 mils thick when cast was crosslinked over a 48 hour period at ambient room temperature conditions as described for the first film. This hydrogel polymer film had a water absorbency 20.7 times its weight and a water solubility of 1 weight percent by the same procedure previously described.

The results obtained in this experiment indicate that an increase in the isocyanato to hydroxyl equivalent ratio to 1.6:1 produced hydrogel polymer films having somewhat lower water absorbency than the films obtained in Examples 3 and 4 and that the hydrogel polymer films were less soluble than films obtained in the previous examples.

EXAMPLE 6

A solution of 200 grams of a poly(oxyethylene) diol having an average molecular weight of 8565 and 1.19 grams of the same triol used in Example 2 was prepared in 835 grams of toluene. The resulting solution was azeotropically distilled and 56 grams of distillate were removed. Analysis of the residual solution indicated a water content of 0.003 weight percent. The dried solution was calculated to contain 177.8 grams of the diol, 1.06 grams of the triol and 526 grams of toluene. A solution of 6.29 grams of methylene bis(4-phenylisocyanate) in 125.7 grams of anhydrous toluene and two drops of dibutyltin dilaurate were added, the isocyanato to hydroxyl equivalent ratio was 1.2:1 and the diol to triol molar ratio was 23.4:1. After stirring at 70°–78° for 50 minutes an additional 323 grams of anhydrous toluene was added to reduce the solids content to 17.9%. Analysis indicated an isocyanato equivalent weight of 530,900 for the solution. Films of about 50 mils thickness were cast on glass plates and cured by exposure to atmospheric moisture under ambient room conditions for 20.75 hours to produce a lightly crosslinked hydrogel. At the end of this period 2 of the plates were vacuum oven dried for 3.5 hours to remove all trace of residual toluene. The other cast films were left at atmospheric conditions. The vacuum dried hydrogel films were tough, opaque and free of toluene odor and had a water absorption capacity equal to 45 times their weight; they were soluble in water to the extent of 38.5 weight percent. The films which were not vacuum dried were also tough and opaque but they had a slight toluene odor. These films showed a water absorption capacity of 32.5 times their weight and were soluble to the extent of 45 weight percent in water.

EXAMPLE 7

An isocyanato terminated prepolymer was prepared in the same manner as described in Example 6 using as the solvent purified methyl ethyl ketone having a 0.0021 percent water content. The reaction was carried out for 1.5 hours at 65°–80°C. using six drops of dibutyltin dilaurate as the catalyst. At the end of this time an additional portion of the diisocyanate was added to bring the total isocyanato to hydroxyl equivalents ratio to 1.4:1 and the mixture was heated at 41°–50°C. for 35 minutes and then allowed to stand overnight at room temperature under nitrogen. The next morning the solidified mixture was heated to 61° to 69° and an additional portion of the diisocyanate was added to bring the total isocyanato to hydroxyl equivalents ratio to 1.78:1. The solution was heated for an additional hour at 60°–67°C. and analysis indicated an isocyanate equivalent weight of 102,600 for the solution. The course of the experiment indicate that an unknown impurity was present that had destroyed some of the diisocyanate. Films of 50 mil thickness were cast on 9 glass plates and the plates were treated as follows:

Group A — This group, containing three plates, was cured for 18 hours at 60°C. in a forced air oven that also contained a beaker of water. By this treatment a tough heterogeneous odor-free hydrogel polymer film was produced which had a water absorption capacity of 38.7 times its weight and a solubility in water of 26.5 weight percent at room temperature.

Group B — The films in this group, consisting of six plates, were lightly crosslinked to the hydrogel polymer by exposure to atmospheric moisture at ambient room conditions for 22.5 hours. These films were difficult to remove from the glass and had an odor of methyl ethyl ketone. They were therefore placed in a vacuum oven at 40°C. for 2 hours to remove residual solvents. The dried films showed a water absorption capacity of 27.7 times their weight and a water solubility of 22 weight percent.

EXAMPLE 8

A mixture was prepared containing 200 grams of a poly(oxyethylene) diol having an average molecular weight of about 19,965, 0.4998 gram of a poly(oxyethylene) triol having an average molecular weight of about 1,190 and 904 grams of benzene. The mixture was azeotropically distilled to remove 73.8 grams of distillate and the residual solution was found to contain 0.0026 weight percent of water. This solution contained 180.42 grams of the diol, 0.451 gram of the triol and 549 grams of benzene; it had a diol to triol molar ratio of 23.8:1. A solution of 3.15 grams of methylene bis(4-phenylisocyanate) in 118 grams of benzene and 2 drops of dibutyltin dilaurate were added and the mixture was stirred at reflux for 15 minutes. The isocyanato to hydroxyl equivalent ratio was 1.2:1 but analysis indicated that all of the diisocyanate had reacted. A sample film cast from this solution was completely soluble indicating that a hydrogel had not been produced. An additional total amount of 1.46 grams of the diisocyanate and 200 grams of benzene were added and the mixture was heated for an additional 1.75 hours at reflux. At this point analysis indicated an isocyanate equivalent weight of 185,500 for the solution. The reaction mixture was diluted with an additional 400 ml. of benzene and 9 films of approximately 50 mils thickness were cast on glass plates.

Group A — Three of the films were crosslinked in a 60° oven for 5¼ hours. There was present in the oven a beaker of water. The cured hydrogel films were slightly yellow and when rolled in water in a glass jar for 8 hours showed a water absorption capacity equal to 45 times their weight and they were soluble to the extent of 21.5 percent.

Group B — The six plates in this group were allowed to stand and cure with the atmospheric moisture at room conditions for about 22 hours. The hydrogel films were tough but had a slight benzene odor, therefore, they were dried in a vacuum oven at 41°C. for 5.25 hours. These hydrogel cast films absorbed 33.6 times their weight of water and were soluble to the extent of 8.5 percent.

EXAMPLE 9

An isocyanato terminated prepolymer was prepared as described in Example 3 by charging 178 grams of a poly(oxyethylene) diol having an average molecular weight of 8565, 1.06 grams of the triol of Example 8 and 7.72 grams of methylene bis(4-phenylisocyanate), all dissolved in 747 grams benzene. The polyol benzene solution was found to contain 0.0073 weight percent of water. The isocyanato to hydroxyl equivalent ratio was 1.3:1. The isocyanato terminated prepolymer was found to have an isocyanate equivalent weight of 67,900 for the solution. Films having a thickness of 50 mils were cast on glass plates. They were placed in a chamber having a constant temperature of 50°C. and constant humidity of 50 percent. Specimens were removed at fixed times and immediately placed in a vacuum oven and dried at 46°C. at full vacuum for 17 hours. In addition to the films indicated above, two of the cast films were cured by allowing them to stand at ambient room conditions for 24 hours to effect crosslinking with atmospheric moisture.

The hydrogel films produced were evaluated for their water absorption capacity and solubility. The results are tabulated below:

| Cure Conditions | Water Absorption Capacity, Times The Weight Of The Film | Water Solubility % |
|---|---|---|
| 10 minutes/chamber | 26 | 14.0 |
| 15 minutes/chamber | 27.2 | 8.5 |
| 20 minutes/chamber | 28.1 | 6.0 |
| 30 minutes/chamber | 31.4 | 8.5 |
| 24 hours ambient room | 33.1 | 10.0 |

The results in this experiment show that one can produce a hydrogel at a rapid rate at a high relative humidity and at a temperature of about 50°C. that will have essentially the same degree of water absorption capacity as is obtained by exposure of the isocyanato terminated prepolymer to ambient conditions for a much longer period of time.

EXAMPLE 10

An isocyanato terminated prepolymer was prepared by reacting 181.71 grams of poly(oxyethylene) diol having an average molecular weight of about 8330, 1.08 grams of a poly(oxyethylene) triol having an average molecular weight of about 1190 and 7.74 grams of methylene bis(4-phenylisocyanate) in 762 grams of benzene at a reflux temperature using 100 ppm of dibutyltin dilaurate catalyst based on the reactants charged. The water content in the polyol benzene mixture was found to be 0.0039 weight percent and the isocyanato to hydroxyl equivalent ratio was 1.3:1. The prepolymer solution was found to have an isocyanate equivalent weight of 76,500.

The prepolymer was converted to a powder hydrogel by the dropwise addition of sufficient n-hexane, while stirring vigorously, to approach the cloud point. At this point a 252 gram portion of the mixture was removed and then the n-hexane addition was continued to the remaining prepolymer solution until a fine white powder began to precipitate. A solution of 0.073 gram of ethylene diamine in 165 ml. of n-hexane was rapidly added to the vigorously stirred prepolymer mixture and immediately a white precipitate formed. Stirring was continued for another 10 minutes and then the slurry was permitted to settle and the supernatant solution was decanted. The solid was washed with three 400 ml. portions of anhydrous n-hexane by pouring the hexane on to the powder, stirring for 5 minutes, letting the solids settle and then decanting. After the last wash the hexane-powder slurry was filtered on a Buchner funnel and the hydrogel powder was spread out and allowed to dry at ambient room conditions over night. The next day the solid was dried to constant weight in a vacuum oven at 30°C. for 5 hours and at 51°C. for 1 hour.

Portions of the hydrogel powder were immersed in jars of distilled water and 0.3 N sodium chloride solution, the jars were capped and rolled for 8 hours at ambient conditions. The hydrogel was found to have a water absorption capacity of 33.2 times its weight of distilled water and 30 times its weight of 0.3 N sodium chloride solution. The hydrogel was soluble in water to the extent of 23.5 weight percent.

What we claim is:

1. A water swellable, lightly crosslinked, hydrogel polymer of the isocyanato terminated prepolymer comprising the reaction product of:
   i. a poly(alkyleneoxy) polyol having an average molecular weight up to about 25,000 wherein the alkyleneoxy group contains from two to four carbon atoms, and
   ii. an organic diisocyanate,
   said prepolymer lightly crosslinked with an equivalent amount of a crosslinking agent of the group:
   iii. water or organic polyamine;
   wherein said poly(alkyleneoxy) polyol is a mixture of a major amount of a poly(ethyleneoxy) diol having an average molecular weight of from about 4,000 to about 25,000, and a minor amount of a higher polyol of the group poly(alkyleneoxy) triol or poly(alkyleneoxy) tetrol or aliphatic polyhydroxyl compound of the formula $C_nH_{2n+2-m}(OH)_m$ wherein $n$ has a value of 3 to 6 and $m$ has a value of 3 to 4, or mixtures thereof, said triol or tetrol having an average molecular weight of from about 92 to 5,000, wherein the mole ratio of diol to higher polyol in said mixture is from about 6:1 to 40:1; wherein the equivalents ratio of isocyanato groups to hydroxyl groups is from about 1.2:1 to about 1.6:1; wherein the organic polyamine is a primary or secondary diamine or triamine; and wherein the equivalents of reactive crosslinking groups in said crosslinking agent used is equivalent to the number of equivalents of isocyanato groups present in said prepolymer.

2. The water swellable, lightly crosslinked, hydrogel polymer of claim 1, wherein said poly(alkyleneoxy) polyol is poly(ethyleneoxy) diol having an average molecular weight of from 4,000 to 25,000.

3. The water swellable, lightly crosslinked, hydrogel polymer of claim 1, wherein said poly(alkyleneoxy) polyol is poly(alkyleneoxy) diol having an average molecular weight of from about 6,000 to 20,000.

4. The water swellable, lightly crosslinked, hydrogel polymer of claim 1, wherein said poly(alkyleneoxy) polyol is a mixture of poly(ethyleneoxy) diol having an average molecular weight of from about 6,000 to 20,000 and a poly(ethyleneoxy) triol having an average molecular weight of from about 500 to 1,500, wherein the mole ratio of diol to triol is from about 15:1 to about 30:1.

5. The water swellable, lightly crosslinked, hydrogel polymer of claim 1, wherein said organic diisocyanate is tolylene diisocyanate.

6. The water swellable, lightly crosslinked, hydrogel polymer of claim 2, wherein said organic diisocyanate is tolylene diisocyanate.

7. The water swellable, lightly crosslinked, hydrogel polymer of claim 3, wherein said organic diisocyanate is tolylene diisocyanate.

8. The water swellable, lightly crosslinked, hydrogel polymer of claim 4, wherein said organic diisocyanate is tolylene diisocyanate.

9. The water swellable, lightly crosslinked, hydrogel polymer of claim 1, wherein said organic diisocyanate is methylenebis(4-phenylisocyanate).

10. The water swellable, lightly crosslinked, hydrogel polymer of claim 2, wherein said organic diisocyanate is methylenebis(4-phenylisocyanate).

11. The water swellable, lightly crosslinked, hydrogel polymer of claim 3, wherein said organic diisocyanate is methylenebis(4-phenylisocyanate).

12. The water swellable, lightly crosslinked, hydrogel polymer of claim 4, wherein said organic diisocyanate is methylenebis-(4-phenylisocyanate).

13. The water swellable, lightly crosslinked, hydrogel polymer of claim 1, wherein said crosslinking agent is water.

14. The water swellable, lightly crosslinked, hydrogel polymer of claim 4, wherein said crosslinking agent is water.

15. The water swellable, lightly crosslinked, hydrogel polymer of claim 5, wherein said crosslinking agent is water.

16. The water swellable, lightly crosslinked, hydrogel polymer of claim 8, wherein said crosslinking agent is water.

17. The water swellable, lightly crosslinked, hydrogel polymer of claim 9, wherein said crosslinking agent is water.

18. The water swellable, lightly crosslinked, hydrogel polymer of claim 12, wherein said crosslinking agent is water.

19. The water swellable, lightly crosslinked, hydrogel polymer of claim 1, wherein said crosslinking is an organic diamine.

20. The water swellable, lightly crosslinked, hydrogel polymer of claim 1, wherein said crosslinking agent is ethylene diamine.

21. The water swellable, lightly crosslinked, hydrogel polymer of claim 4, wherein said crosslinking agent is ethylene diamine.

22. The water swellable, lightly crosslinked, hydrogel polymer of claim 5, wherein said crosslinking agent is ethylene diamine.

23. The water swellable, lightly crosslinked, hydrogel polymer of claim 8, wherein said crosslinking agent is ethylene diamine.

24. The water swellable, lightly crosslinked, hydrogel polymer of claim 9, wherein said crosslinking agent is ethylene diamine.

25. The water swellable, lightly crosslinked, hydrogel polymer of claim 12, wherein said crosslinking agent is ethylene diamine.

26. The water swellable, lightly crosslinked, hydrogel polymer of claim 1, wherein said crosslinking agent is a mixture of organic diamine and organic triamine.

27. The water swellable, lightly crosslinked, hydrogel polymer of claim 2, wherein said crosslinking agent is a mixture of organic diamine and organic triamine.

28. The water swellable, lightly crosslinked, hydrogel polymer of claim 3, wherein said crosslinking agent is a mixture of organic diamine and organic triamine.

29. The water swellable, lightly crosslinked, hydrogel polymer of claim 6, wherein said crosslinking agent is a mixture of organic diamine and organic triamine.

30. The water swellable, lightly crosslinked, hydrogel polymer of claim 7, wherein said crosslinking agent is a mixture of organic diamine and organic triamine.

31. The water swellable, lightly crosslinked, hydrogel polymer of claim 10, wherein said crosslinking agent is a mixture of organic diamine and organic triamine.

32. The water swellable, lightly crosslinked, hydrogel polymer of claim 11, wherein said crosslinking agent is a mixture of organic diamine and organic triamine.

33. The water swellable, lightly crosslinked, hydrogel polymer of claim 1, wherein the crosslinking agent is a mixture of ethylene diamine and diethylene triamine.

34. The water swellable, lightly crosslinked, hydrogel polymer of claim 2, wherein the crosslinking agent is a mixture of ethylene diamine and diethylene triamine.

35. The water swellable, lightly crosslinked, hydrogel polymer of claim 3, wherein the crosslinking agent is a mixture of ethylene diamine and diethylene triamine.

36. The water swellable, lightly crosslinked, hydrogel polymer of claim 6, wherein the crosslinking agent is a mixture of ethylene diamine and diethylene triamine.

37. The water swellable, lightly crosslinked, hydrogel polymer of claim 7, wherein the crosslinking agent is a mixture of ethylene diamine and diethylene triamine.

38. The water swellable, lightly crosslinked, hydrogel polymer of claim 10, wherein the crosslinking agent is a mixture of ethylene diamine and diethylene triamine.

39. The water swellable, lightly crosslinked, hydrogel polymer of claim 11, wherein the crosslinking agent is a mixture of ethylene diamine and diethylene triamine.

40. The water swellable, lightly crosslinked, hydrogel polymer of claim 1, wherein said poly(alkyleneoxy) polyol is poly(ethyleneoxy) diol, said organic diisocyanate is tolylene diisocyanate, and said crosslinker is a mixture of ethylene diamine and diethylene triamine.

41. The water swellable, lightly crosslinked, hydrogel polymer of claim 1, wherein said poly(alkyleneoxy) polyol is poly(ethyleneoxy) diol, said organic diisocyanate is methylenebis(4-phenylisocyanate), and said crosslinker is a mixture of ethylene diamine and diethylene triamine.

42. The water swellable, lightly crosslinked hydrogel, polymer of claim 1, wherein said poly(alkyleneoxy) polyol is a mixture of poly(ethyleneoxy) diol and poly(ethyleneoxy) triol, said organic diisocyanate is tolylene diisocyanate, and said crosslinker is water.

43. The water swellable, lightly crosslinked hydrogel, polymer of claim 1, wherein said poly(alkyleneoxy) polyol is a mixture of poly(ethyleneoxy) diol and poly(ethyleneoxy) triol, said organic diisocyanate is methylene bis(4-phenylisocyanate), and said crosslinker is water.

44. The water swellable, lightly crosslinked hydrogel, polymer of claim 1, wherein said poly(alkyleneoxy) polyol is a mixture of poly(ethyleneoxy) diol and poly(ethyleneoxy) triol, said organic diisocyanate is tolylene diisocyanate, and said crosslinker is ethylene diamine.

45. The water swellable, lightly crosslinked, hydrogel polymer of claim 1, wherein said poly(alkyleneoxy) polyol is a mixture of poly(ethyleneoxy) diol and poly(ethyleneoxy) triol, said organic diisocyanate is methylenebis(4-phenylisocyanate), and said crosslinker is ethylene diamine.

* * * * *